(12) United States Patent
Salzburger et al.

(10) Patent No.: US 8,677,826 B2
(45) Date of Patent: Mar. 25, 2014

(54) METHOD FOR EVALUATING RECEIVED SIGNALS ACQUIRED DURING A NON-DESTRUCTIVE ULTRASONIC WAVE TEST, AND DEVICE FOR NON-DESTRUCTIVE ULTRASONIC WAVE TESTING OF A TEST BODY

(75) Inventors: Hans-Jürgen Salzburger, Neunkirchen (DE); Frank Niese, Saarbrücken (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 187 days.

(21) Appl. No.: 13/054,165

(22) PCT Filed: Jul. 16, 2009

(86) PCT No.: PCT/EP2009/005188
§ 371 (c)(1),
(2), (4) Date: Apr. 13, 2011

(87) PCT Pub. No.: WO2010/006797
PCT Pub. Date: Jan. 21, 2010

(65) Prior Publication Data
US 2011/0179875 A1  Jul. 28, 2011

(30) Foreign Application Priority Data
Jul. 16, 2008 (EP) .................................. 08012873

(51) Int. Cl.
*G01N 29/04* (2006.01)

(52) U.S. Cl.
USPC .................................. 73/643; 73/598; 73/602

(58) Field of Classification Search
CPC ....................................................... G01N 29/075
USPC ............ 73/622, 643, 507, 598, 599, 600, 632
See application file for complete search history.

(56) References Cited

U.S. PATENT DOCUMENTS

| | | | | |
|---|---|---|---|---|
| 4,471,658 | A * | 9/1984 | Morimoto | 73/643 |
| 5,359,898 | A * | 11/1994 | Latimer | 73/600 |
| 5,456,113 | A * | 10/1995 | Kwun et al. | 73/587 |
| 5,811,682 | A * | 9/1998 | Ohtani et al. | 73/643 |
| 6,164,137 | A * | 12/2000 | Hancock et al. | 73/643 |
| 6,170,336 | B1 * | 1/2001 | Johnson et al. | 73/643 |
| 6,766,694 | B2 * | 7/2004 | Hubschen | 73/643 |
| 6,920,792 | B2 * | 7/2005 | Flora et al. | 73/622 |
| 7,395,715 | B2 * | 7/2008 | Salzburger et al. | 73/643 |
| 7,426,867 | B2 * | 9/2008 | Koch et al. | 73/627 |
| 7,434,467 | B2 * | 10/2008 | Hubschen et al. | 73/643 |
| 7,697,375 | B2 * | 4/2010 | Reiderman et al. | 367/168 |

\* cited by examiner

*Primary Examiner* — J M Saint Surin
(74) *Attorney, Agent, or Firm* — Antonelli, Terry, Stout & Kraus, LLP.

(57) ABSTRACT

A method and device are disclosed for evaluating received signals acquired during non-destructive ultrasonic testing of a test body, wherein ultrasound waves are generated inside the test body with an electromagnetic ultrasonic transducer acting as an ultrasound transmitter and ultrasound waves which propagate within the test body are converted into received signals with an electromagnetic ultrasonic transducer acting as an ultrasound receiver. The received signals are evaluated for the purpose of examining the test body.

15 Claims, 4 Drawing Sheets

METHOD FOR EVALUATING RECEIVED SIGNALS ACQUIRED DURING A NON-DESTRUCTIVE ULTRASONIC WAVE TEST, AND DEVICE FOR NON-DESTRUCTIVE ULTRASONIC WAVE TESTING OF A TEST BODY

BACKGROUND OF THE INVENTION

1. Field of the Invention

The invention relates to a method and device for evaluating received signals acquired during a non-destructive ultrasonic wave test on a test body.

2. Description of the Prior Art

Electromagnetic ultrasonic probes, EMUS probes for short, are used in a manner known per se for the non-destructive examination or measurement of test objects, which possess at least electrically conductive and ferromagnetic material parts, and are capable of generating and also detecting, free from coupling means, elastic waves inside a test object. From the large number of different embodiments of such probes, reference is made to DE 26 55 904 B2 and DE 195 43 481 C2 as being representative.

The working principle underlying the EMUS probes is based on the provision of an electric coil with a predetermined geometry and number of turns, which is acted upon by a high frequency (HF) current pulse or also a burst signal, the mid-frequency whereof corresponds to the frequency of ultrasound waves that is generated in a desired manner inside the test object. The HF current pulse thus induces within the skin depth of an electrically conductive (preferably homogeneous medium located close to the electric coil) electric eddy currents the two-dimensionally extending distribution whereof within the skin depth being mirror-inverted to the geometry of the coil area. If a static or almost static magnetic field is superimposed on the eddy currents induced inside the medium, with magnetic field lines orientated parallel to the material surface or normal to the latter, spatial and temporally periodic elastic displacements in the form of elastic waves in the frequency range of the ultrasound are generated inside the medium. The displacements are capable of being duly propagated inside the medium.

Conversely, an elastic wave arriving at the site of the electric coil generates, in the presence of a stationary or almost stationary magnetic field, an electrical field proportional to the displacement speed and the magnetic induction, as a result of which a proportional electric voltage is induced in the coil. This mechanism for generating electrical signals from elastic wave pulses can be used for the detection of ultrasound waves by using EMUS probes. However, the signal levels of the voltage pulses generated in this way lie in the μV range, so that a strong and low-noise pre-amplification is required in order to obtain, as far as possible, signal levels that can be evaluated. Furthermore, the pre-amplified signal levels are subjected to electrical filtering with as narrow a band as possible in order to improve the signal-to-noise ratio.

Due to its electrical inductivity, however, the coil is also capable of receiving electromagnetic signals other than those which, as described above, originate from the elastic wave pulses. In addition, there is the fact that the impedance of the coil is designed with as high a resistance as possible in order to generate voltage signal levels as high as possible. Both factors mean that EMUS probes also, apart from detecting voltage signals originating from ultrasound waves, detect signals which originate from externally inductively acting electromagnetic signal sources. The latter run through the same amplification and, as the case may be, filter chain as the ultrasound signals and cannot be readily distinguished from the ultrasound signals.

SUMMARY OF THE INVENTION

The invention is a method and device for evaluating received signals acquired during a non-destructive ultrasonic wave test on a test body, wherein ultrasound waves are generated inside the test body with an electromagnetic ultrasonic transducer acting as an ultrasound transmitter and ultrasound waves that propagate within the test body are converted into a form of useful signals with an electromagnetic ultrasonic transducer acting as an ultrasound receiver. The useful signals are evaluated for the purpose of examining the test body, in such a way that it should be possible to select interference signals from the detected received ultrasound signals, so that a reliable evaluation is possible solely on the basis of genuine received ultrasound signals.

The method and device according to the invention for suppressing or eliminating interfering received signals, which are picked up by a receiving probe through conductive interaction, use two electromagnetic ultrasound receivers with reception coils assigned respectively thereto being disposed spatially offset with respect to one another by one-half of a wavelength, and wherein the ultrasound waves are coupled into the test body by the ultrasound transmitter. The reception coils are identical in their geometrical and electrical properties and on the basis of inductive interaction generate independent voltage signals which are subsequently processed separately.

The aforementioned requirement regarding the two ultrasound receivers is not necessarily to be understood to mean that two separate EMUS probes have to be disposed in the immediate spatial vicinity on the test body. On the contrary, it is essentially a matter of ensuring that two separate reception coils are used in the aforementioned manner, which are incorporated into a common coil carrier, for reasons of making a straightforward technical implementation possible. To this extent, two EMUS probes are incorporated in a common type of construction in a preferred example of an embodiment of the invention.

The received signals which are detected by each individual reception coil first have to be subjected to a pre-amplification and preferably a bandpass filtering, before the received signals are converted into the form of digital ultrasound signals by an analog/digital conversion and stored in two data sets.

In a further process step, phases $\phi 1(t)$ and $\phi 2(t)$ corresponding to the two received signals are calculated. The notation $\phi 1(t)$ and $\phi 2(t)$ expresses the fact that a value describing the phase position at each time t is calculated for each of the received signals stored in the two data sets. That is $\phi 1(t)$ corresponds to the phase positions of all the received signals stored in the first data set and $\phi 2(t)$ to the phase positions of all the received signals stored in the second data set.

A common phase reference point is required for the calculation of the phases $\phi 1(t)$ and $\phi 2(t)$, especially since the subsequent signal evaluation relates to each other by the phase positions of the received signals of the two data sets. The trigger time at which the analog/digital conversion is initiated in terms of time is preferably selected as a common phase reference point. Alternatively, it may be advisable to select as phase reference points individual or several trigger times which synchronize the data recording of the digitalized received signals with respect to each other.

The data recording of the digitalized received signals, which respectively originate from the two reception coils, typically takes place at a fixedly preselected data or sample rate, such as for example 10 MHz. The recording duration, which ultimately establishes the depth from which ultrasound signals are acquired from the test body, is selected according to the given test body and the defined test task. In addition, it is advantageous to select a common phase reference point for all the received signals received within the recording duration.

In a further process step, the phase difference of synchronous received signals from both data sets is determined for each individual time-related sampling point, on the basis of which phase difference a selection of the received signals from the first and second data set of received signals is carried out according to the following requirement:

If the phase difference $\phi(t)$ of two synchronous received signals under consideration lies in the range $[180°-\alpha^-; 180°+\alpha^+]$ with $\alpha^-$; $\alpha^+$ in each case less than 15°, a selection of these received signals from all the remaining received signals takes place. A further evaluation of the received signals takes place on the basis of the received signals selected above.

The method and device according to the invention are based on the knowledge that inductively coupled interference signals in both reception coils originating from external signal sources have varying phase positions with respect to one another, which fluctuate between 0° and 360°, but do not have a phase difference of OM in the range $[180°-\alpha^-; 180°+\alpha^+]$, whereas the useful signals originating from the ultrasound signals provide, due to the local offset of the two reception coils, a phase difference $\phi(t)$ in the range $[180°-\alpha^-; 180°+\alpha^+]$ over the whole signal length. The method according to the invention therefore offers the possibility of separating interference and ultrasound signals from one another by the targeted evaluation of the phase positions of the received signals detected by two reception coils.

For the straightforward implementation of the method according to the invention, use is made of a device which provides two electromagnetic ultrasonic transducers acting as ultrasound receivers, each with a reception coil. The coil geometry and number of turns are identical, and both coil arrangements are disposed spatially offset with respect to one another by one half of a wavelength, of the ultrasound waves excited inside the test body by the ultrasound transmitter. Furthermore, a received signal evaluator unit, evaluates the received signals of both ultrasound receivers in the aforementioned manner. For this purpose, the received signal evaluation unit provides, for each ultrasound receiver, a pre-amplifier and an analog/digital converter for acquiring digitalized time signals of the received signals received per ultrasound receiver. The time signals, in the form of A scans, are stored as a data set per ultrasound receiver by a memory unit. A computer finally performs the evaluation of both A scans according to the aforementioned method.

As already stated above, both ultrasound receivers comprise, in a particularly preferred embodiment, a common coil carrier, on which the reception coils of both ultrasound receivers are wound. The coil carrier can be made from a dielectric or from a metallic material.

The method and device for providing implementation of the invention are explained in greater detail below with the aid of specific examples of embodiment.

BRIEF DESCRIPTION OF THE DRAWINGS

The invention is described below, by way of example and without restriction thereof, with the aid of examples of an embodiment making reference to the drawings. In the figures.

WAYS OF PERFORMING THE INVENTION, INDUSTRIAL APPLICABILITY

Figure 1:
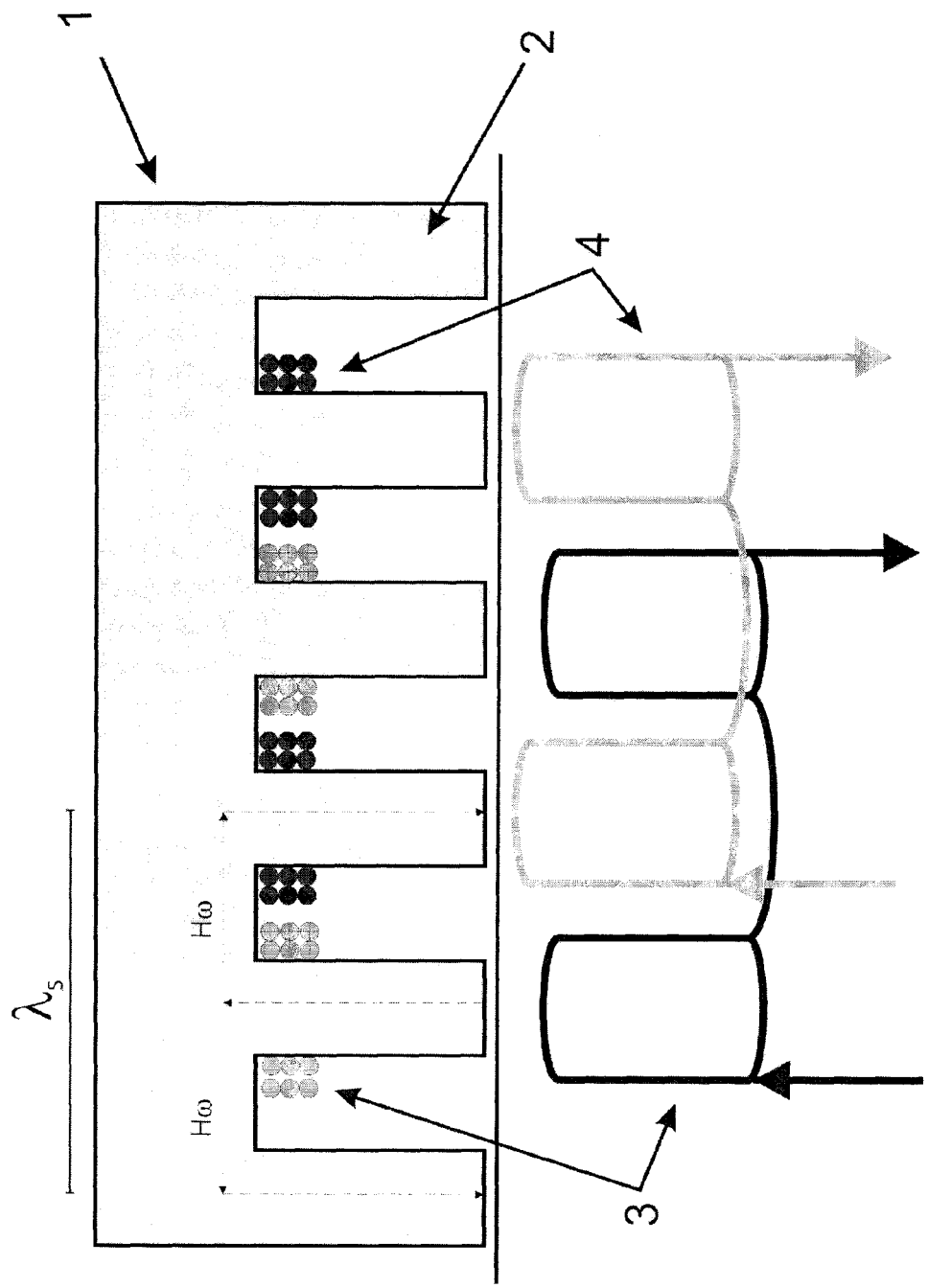
FIG. 1 shows a schematic structure of an EMUS probe with two reception coils disposed spatially offset with respect to each other.

FIG. 1 represents an EMUS probe in a side view as a sectional drawing, which comprises a comb coil carrier 1, which can be made from a dielectric or from a metallic material. Around the comb structures 2, with an ending open at one side, two coil windings 3 and 4 are disposed offset with respect to one and another by one-half of wavelength $\lambda_s$, of the ultrasound waves to be detected from a test body. The coil windings surrounding the comb structures 2 are a web according to the winding plan shown in the lower view of FIG. 1. With the aid of an EMUS probe, ultrasound waves are detected from a test body (not represented in any further detail). The received signals received by coils 3 and 4 are detected and stored separately from one another. The two reception coils 3 and 4 are designed electrically and geometrically to be identical and have only a mutual spacing of ½λ related to the ultrasound wavelength of the ultrasound waves to be detected.

Figure 2:
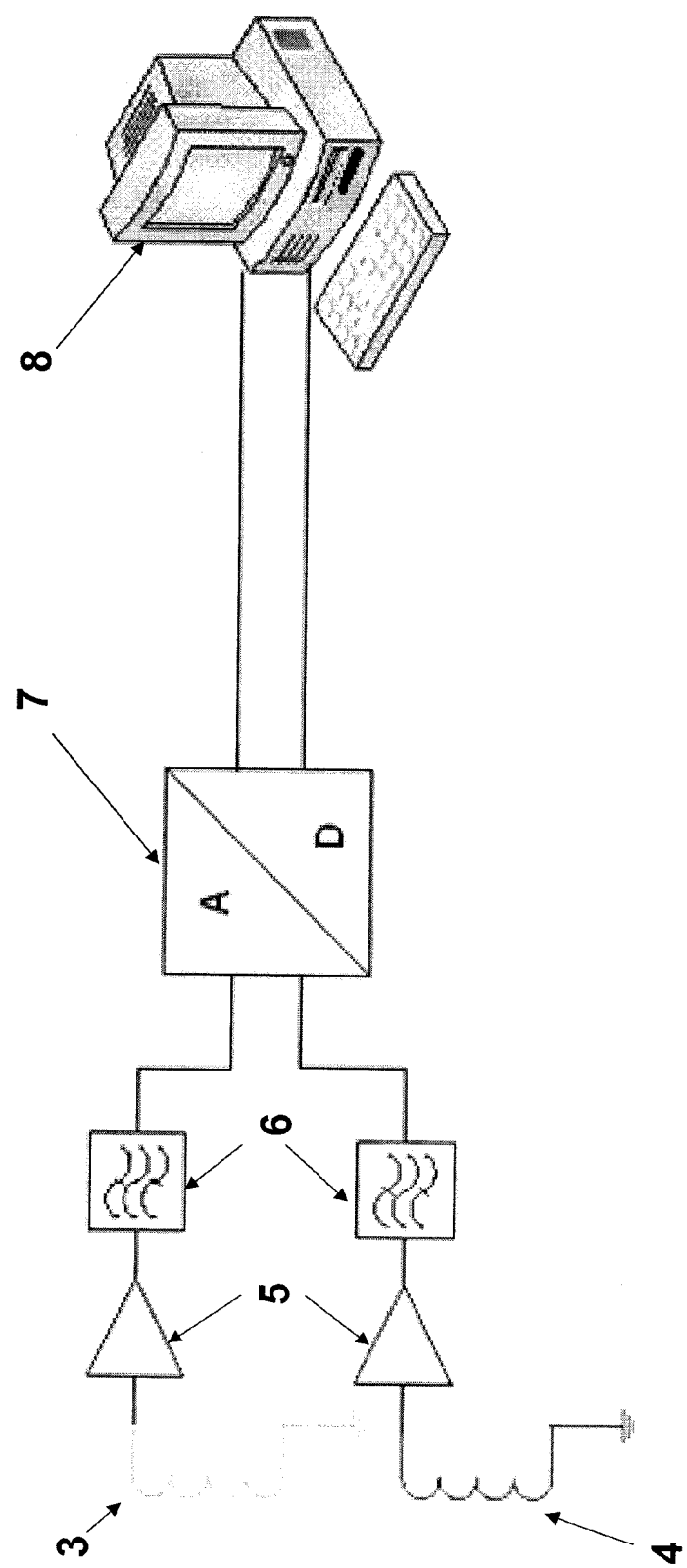
FIG. 2 shows a test data acquisition and evaluation system.

The test data acquisition and evaluation system illustrated in FIG. 2 is used for the signal evaluation of the received signals which are received by the two separate reception coils 3 and 4. The received signals provided by the reception coils 3 and 4 are pre-processed by a pre-amplifier 5 and a subsequent bandpass filter unit 6 and are then converted into digitalized received signals by a two-channel analog-digital converter unit 7 and passed on for further evaluation by a computer 8. The evaluation provided by computer unit 8 essentially takes place in four processing steps:

A calculation of the phase position of each individual received signal at each time t first takes place at a suitably selected phase position reference point which, as explained above, is preferably the trigger time for the analog-digital conversion with subsequent storage of the received signals originating from both reception coils. Two data sets of received signals are respectively assigned phase information.

In a second step, the phase differences of synchronous received signals are determined from both data sets.

In a third step, an enquiry takes place to determine whether the phase difference of the synchronous received signals lies within a given value range, that is, in the range $[180°-\alpha^-; 180°+\alpha^+]$ with $\alpha^-$, $\alpha^+$ in each case being less than 15°.

In the fourth step, a selection of the received signals takes place in such a way that only received signals are selected which meet the aforementioned condition. All the other received signals, on the other hand, are preferably set equal to zero. With the latter mentioned measure, all acquired received signal segments which do not exhibit the criterion characteristic of useful signals, that is a difference of the signal phases of both received signals that is constant over several periods, are set equal to zero and thus filtered out. Since the selection algorithm is independent of the level and the differences in amplitudes of the two received signals, incoherent signals with low signal levels are also filtered out, as a result of which the invention can also be used with noisy signals with a low signal-noise ratio. The filter algorithm basically leaves the signal amplitudes unchanged, so that the filtered-out useful signals can be treated according to established criteria of the amplitude evaluation.

The example of an embodiment of an EMUS probe coil represented in FIG. 1 can be used both in a magnetic field orientated vertically as well as horizontally to the material surface of a test body and can be used, moreover, for the reception of ultrasound waves striking the surface obliquely from the interior of the material, that is with transverse waves with vertical and horizontal polarization, as well as ultrasound waves propagating at the surfaces, such as for example Rayleigh surface waves and horizontally polarized transverse waves.

Figure 3:
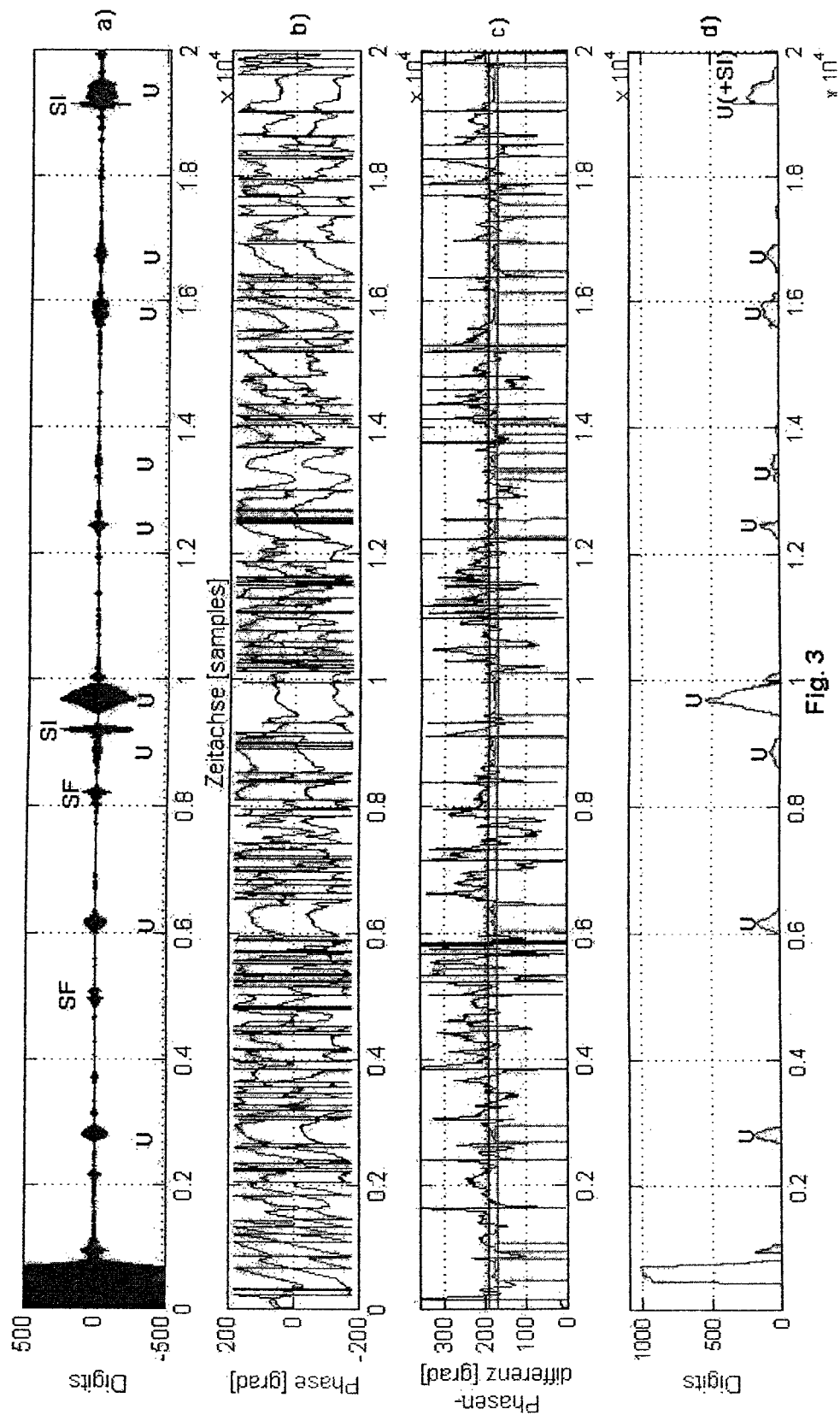
FIG. 3 shows a diagrammatic representation of received signals on a test wheel functioning as a test body.

FIG. 3 represents a compilation of individual diagrams representing the received signals as well as the reception magnitudes derived therefrom, which are used to explain the method according to the invention. Thus, the A scan according to the upper diagrammatic representation illustrated in FIG. 3 represents the measurement result of a static measurement on a wheel set, into the tread whereof a test fault in the form of a saw cut is introduced. In addition, there are two further real faults in the form of two incipient cracks inside the tread which proceed from the running edge. The reflection signals, marked in each case with "U", originate from ultrasound signals, which represent direct echoes or successive echoes of the previously described actual material faults. The signals marked in the A scan with SF and SI, on the other hand, were deliberately induced in the reception coils as electromagnetic interference pulses by an electric hairdryer and a flat-spiral coil subjected to a voltage pulse.

The uppermost diagram a) represents an A scan, which represents the received signals along the time axis with sample points from 0 to 20,000 being plotted along the time axis. Local amplitude overshoots present along the time axis mark potential reflection events inside a test body, although the latter can also originate from external signal sources in the sense of interferences.

The received signals represented in the A scan according to the upper diagrammatic representation a) were obtained with two reception coils described above according to the example of embodiment in FIG. 1 and were each are digitalized separately from each other at a sample rate of 10 MHz following pre-amplification and bandpass filtering. The received signals of the two reception coils overlap on the basis of the illustrated A scan and, on the basis of the upper diagram, cannot be distinguished from one another visually. Diagram b) shown directly beneath the upper diagram illustrates the phase positions ascertained by calculation from the digitalized received signals of the two reception channels, in each case related to a common phase reference point. Diagram b) shows only qualitatively that the phase positions of the received signals, which originate from the two reception coils, appear clearly recognizable by the two separate function courses which are represented along the time axis in diagram b).

It can be seen that the phase positions $\phi_1(t)$, $\phi_2(t)$ of the respective received signals lie between $-180°$ and $+180°$. The ascertained phase difference $\phi(t)$ between the phase positions of the two received signals is indicated in diagram c) third from the top, also plotted along the time axis. All the received signal components whose phase difference $\phi(t)$ lies within the range $[180°-\alpha^-; 180°+\alpha^+]$ with $\alpha^-$, $\alpha^+ < 15°$ are of particular interest here; this is highlighted pictorially by the two lines in the diagram drawn horizontally. All the received signal components whose phase difference $\phi(t)$ lies within the range denoted above are classified as useful signals. All other signal segments that do not satisfy this criterion are classified as interference signals and are set equal to zero.

Bottom diagram d) represents the envelope of all signal components which satisfy the aforementioned criterion of an ultrasound useful signal. All other signal components are set to zero.

Reference should once again be made to the upper diagram, which represents the A scan and shows reflection signals which are marked with U, SF and SI.

Figure 4:
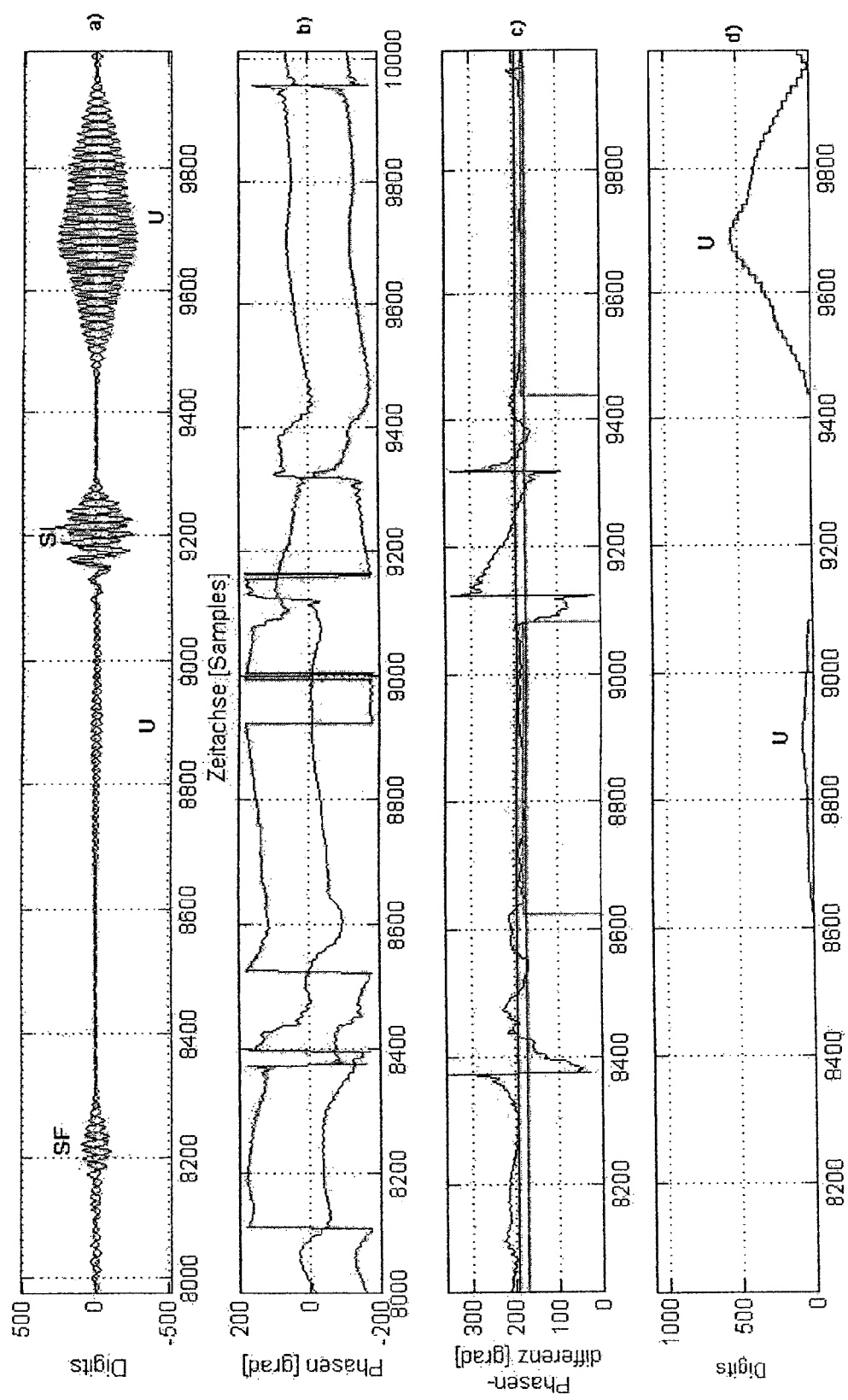
FIG. 4 shows an enlarged detailed representation of a reception sequence represented in FIG. 3.

On the basis of the diagram compilation in FIG. 4, which shows a scaled enlargement of a section of the diagrams shown in FIG. 3 (see the area in FIG. 3 drawn using broken lines), that is an enlarged representation of all the received signals in the time range between 8000 and 10,000 sample points, makes it possible to determine, by making reference to diagram b) second from the top, the phase shift of the received signals originating from the two reception coils. The interference signals marked with SF and SI are out of phase over a signal duration containing approx. 6 to 7 periods, and moreover with a continuously changing phase difference. In contrast, the phase difference $\phi(t)$ of the ultrasound signals marked with U is relatively constant equal to 180°.

The calculated phase difference OM of the received signals is also represented as enlarged in diagram c) represented thereunder. Thus, it can be seen that the phase difference $\phi(t)$ in the areas marked with x and y amounts constantly to approx. 180°. As mentioned above, this corresponds to the actual useful signals which are represented as envelope U in bottom diagram d). In all other areas in which this criterion is not satisfied, the corresponding interference signal components are set equal to zero. Signals SF and SI therefore no longer appear in the bottom evaluation diagram.

LIST OF REFERENCE NUMBERS 1 coil carrier
2 comb-like structure
3 reception coil
4 reception coil
5 pre-amplifier
6 bandpass filter unit
7 analog-digital converter
8 computer unit

The invention claimed is:

1. A method for evaluating received signals acquired during non-destructive ultrasonic testing of a test body, wherein ultrasound waves are generated inside the test body by an electromagnetic ultrasonic transducer functioning as an ultrasound transmitter and the ultrasound waves within the test body are detected as received signals by an electromagnetic ultrasonic transducer functioning as an ultrasound receiver and the received signals are evaluated to examine the test body, comprising:

converting the ultrasound waves within the test body with electromagnetic ultrasonic transducer-receivers disposed spatially offset, with respect to each other by one-half of a wavelength of the ultrasound waves transmitted within the test body ultrasound transmitter, to obtain a first and a second data set of received signals;

calculating phases $\phi1(t)$ and $\phi2(t)$, corresponding to the received signals of the first and second data sets;

determining a phase difference $\phi(t)=\phi1(t)-\phi2(t)$;

selecting received signals from the first and the second data sets of received signals, wherein the phase difference $\phi(t)$ is in a range between $(180°-\alpha-)$ and $(180°+\alpha+)$ with $\alpha-$ and $\alpha+ <15°$; and evaluating the selected received signals.

2. The method according to claim 1, wherein the received signals generated by the ultrasound receiver are pre-amplified, digitally converted and stored.

3. The method according to claim 2, wherein a trigger time for digital data conversion is used as a phase reference point.

4. The method according to claim 1, wherein the received signals generated by the ultrasound receiver are pre-amplified, bandpass filtered, digitally converted and stored.

5. The method according to claim 4, wherein a trigger time for digital data conversion is used as a phase reference point.

6. The method according to claim 4 wherein the pre-amplified and, bandpass-filtered received signals from the ultrasonic transducer-receivers are digitally converted by digital conversion at a predetermined sample rate and sample depth and are stored as A scans in a data set, which corresponds to an ultrasonic transducer.

7. The method according to claim 1, wherein a trigger time for digital data conversion is used as a phase reference point.

8. A device for non-destructive ultrasonic testing of a test body comprising:
an electromagnetic ultrasonic transducer functioning as an ultrasound transmitter and an electromagnetic ultrasonic transducer functioning as an ultrasound receiver for converting ultrasound waves propagating within the test body into received signals, including a pair of electromagnetic ultrasonic wave transducers functioning as ultrasound receivers which each include a high frequency (HF) coil of identical coil geometry and turns of each coil being disposed on a different coil carrier, with the HF coils of each transducer being electrically separated and spatially separated from each other on the different coil carriers by a distance of one-half of a wavelength of the ultrasound waves excited inside the test body by the ultrasound transmitter and a received signal evaluator including for each ultrasound receiver a pre-amplifier and an analog to digital converter for obtaining digitalized time signals of the received signals received for the ultrasound receiver, a memory for storing time signals as scans for a data set for each ultrasound receiver and a computer for evaluating the scans.

9. The device according to claim 8, wherein the ultrasound receivers comprise a common coil carrier, on which the HF coils of the ultrasound receivers are wound.

10. The device according to claim 9 wherein the scans are A scans.

11. The device according to claim 9, wherein the coil carrier comprises a dielectric or a metallic material.

12. The device according to claim 11 wherein the scans are A scans.

13. The device according to claim 8, wherein the coil carrier comprises a comb open on one side, around which HF coils are wound.

14. The device according to claim 13 wherein the scans are A scans.

15. The device according to claim 8 wherein the scans are A scans.

* * * * *